United States Patent
Neigel

(10) Patent No.: US 9,687,002 B2
(45) Date of Patent: Jun. 27, 2017

(54) BOTANICAL ANTIMICROBIAL MICROEMULSIONS (BAMM)

(71) Applicant: Dennis Victor Neigel, Salisbury, NC (US)

(72) Inventor: Dennis Victor Neigel, Salisbury, NC (US)

(73) Assignee: Indusco, Ltd., Greensboro, NC (US)

(*) Notice: Subject to any disclaimer, the term of this patent is extended or adjusted under 35 U.S.C. 154(b) by 43 days.

(21) Appl. No.: 14/718,565

(22) Filed: May 21, 2015

(65) Prior Publication Data

US 2016/0338362 A1 Nov. 24, 2016

(51) Int. Cl.
| | |
|---|---|
| A61K 36/00 | (2006.01) |
| A01N 65/22 | (2009.01) |
| A01N 65/24 | (2009.01) |
| A01N 65/36 | (2009.01) |
| A61K 36/53 | (2006.01) |
| A01N 27/00 | (2006.01) |
| A01N 65/08 | (2009.01) |

(52) U.S. Cl.
CPC ............ *A01N 65/22* (2013.01); *A01N 27/00* (2013.01); *A01N 65/08* (2013.01); *A01N 65/24* (2013.01); *A01N 65/36* (2013.01); *A61K 36/53* (2013.01)

(58) Field of Classification Search
None
See application file for complete search history.

(56) References Cited

U.S. PATENT DOCUMENTS

| | | | |
|---|---|---|---|
| 4,835,002 A | 5/1989 | Wolf et al. | |
| 5,376,397 A | 12/1994 | Gaonkar | |
| 5,468,725 A * | 11/1995 | Guenin | A61K 8/062 512/2 |
| 5,719,114 A * | 2/1998 | Zocchi | A01N 53/00 510/102 |
| 5,891,490 A | 4/1999 | Merabet | |
| 6,346,281 B1 | 2/2002 | DeAth et al. | |
| 6,902,756 B2 | 6/2005 | Vlad | |
| 8,417,877 B2 | 4/2013 | Brandt | |
| 8,921,303 B1 * | 12/2014 | Lull | A61L 9/013 424/70.11 |
| 2003/0114345 A1 * | 6/2003 | Leonard | C11D 1/94 510/417 |
| 2007/0161526 A1 * | 7/2007 | Vlad | A61K 8/068 510/130 |

FOREIGN PATENT DOCUMENTS

| | | |
|---|---|---|
| EP | 2460409 | 6/2012 |
| WO | WO 2013/075921 | 5/2013 |

* cited by examiner

*Primary Examiner* — Qiuwen Mi
(74) *Attorney, Agent, or Firm* — Tuggle Duggins P.A.; Blake P. Hurt

(57) ABSTRACT

A method to produce clear, thermodynamically stable Botanical AntiMicrobial Microemulsions (BAMM) made from all edible ingredients is disclosed, as well as their use as highly effective antimicrobial broad spectrum disinfectants/deodorants that are not hazardous to humans or animals.

17 Claims, No Drawings

BOTANICAL ANTIMICROBIAL MICROEMULSIONS (BAMM)

CROSS REFERENCE TO RELATED APPLICATIONS

Not Applicable

STATEMENT REGARDING FEDERALLY SPONSORED RESEARCH OR DEVELOPMENT

Not Applicable

REFERENCE TO SEQUENCE LISTING, A TABLE OR A COMPUTER PROGRAM LISTING COMPACT DISK APPENDIX OR A DESCRIPTION OF DRAWINGS

Not applicable

TECHNICAL FIELD OF THE INVENTION

The present invention relates to a process using naturally derived, food grade, renewable botanical essential oils or extracts processed into crystal clear, stable oil-in-water microemulsions. In particular, the invention relates to the use of such microemulsions as antimicrobial agents that protect a variety of surfaces from microbial growth, without need for concern for human toxicity.

BACKGROUND OF THE INVENTION

A biocide is any substance that kills microorganisms such as bacteria, molds, algae, fungi or viruses. A biostatic is any substance that inhibits the growth of these organisms. The collective group is called antimicrobials. People have been utilizing antimicrobials, commonly called preservatives, since they first discovered a need to extend the useful life of their food as well as their possessions. Sea salt may have been the first antimicrobial used to preserve food. The mummification techniques employed by early Egyptians used to preserve the human and animal body used salts, a variety of resins and the herb Thyme. These preservatives were thought to possess magical powers, as well as the ability to install qualities of eternal life.

The existence of microorganisms in nature was discovered in the late 1600s with the invention of the microscope. As early as 1705, mercuric chloride was used to preserve ships' planking against shipworm. It was not until the 19th century discoveries by Pasteur, Gram and others that the causative agents of microbiological deterioration were understood, although use of antimicrobials in a cause and effect relationship with microorganisms is less than a century old.

A wide range of natural organic compounds are used as antimicrobials. Organic acids are used widely as antimicrobials in food products, e.g. lactic acid, citric acid, acetic acid, and their salts, either as ingredients, or as disinfectants. For example, beef carcasses often are sprayed with acids, and then rinsed or steamed, to reduce the prevalence of *E. coli*.

Traditional healers long have used plants to prevent or cure infectious disease. Many of these plants have been investigated scientifically for antimicrobial activity, and a large number of plant products have been shown to inhibit the growth of pathogenic microorganisms. A number of these agents appear to have structures and modes of action that are distinct from those of the antibiotics in current use, suggesting that cross-resistance with agents already in use may be minimal. So, it is worthwhile to study plants and plant products, such as essential oils and extracts for activity against resistant bacteria, viruses, fungi and mold.

An essential oil is a concentrated hydrophobic liquid containing volatile aroma compounds obtained from the leaves, bark, stems, flowers and berries of plants. Essential oils are also known as volatile oils, ethereal oils, aetherolea, or simply as the "oil of" the plant from which they were extracted, such as oil of thyme. An oil is "essential" in the sense that it carries a distinctive scent, or essence, of the plant, and not that it is essential to life.

Essential oils are generally extracted by distillation, often by using steam. Other processes include expression or solvent extraction, including supercritical $CO_2$. They are used in perfumes, cosmetics, soaps and other products, for flavoring food and drink, for aromatherapy and as natural, renewable antimicrobials.

Many essential oils included in pharmacopoeias possess antimicrobial activity, including but not limited to: oils of bay, cedar, cinnamon, citronella, clove, *eucalyptus*, garlic, geranium, lavender, leleshwa, lemon, lemongrass, mint neem, black cumin, onion, oregano, peppermint, rosemary, sandalwood, sesame, tea tree and thyme.

Essential oils that are listed as edible include: almond oil (bitter), anise oil, bergamot oil, camphor oil, caraway oil, *cassia* oil, cedar leaf oil, cedarwood oil, cinnamon oil, citronella oil, clove oil, cornmint oil (*Mentha arvensis*), *eucalyptus* oil, geranium oil, grapefruit oil, lavender oil (spike), lemon oil, lemongrass oil, lignaloe (bois derose oil), lime oil, neroli (orange lower oil), nutmeg oil, onion and garlic oil, mint oil, orange oil, oregano oil, *origanum* oil, orris oil, palmarosa oil, patchouli oil, peppermint oil (Menthapzperita) pettigrainolpine oil, pine needle oil, rose oil (attar of roses), rosemary oil, sandalwood oil, *sassafras* oil, sesame oil, spearmint oil, thyme oil, vetiver oil, and ylang ylang oil.

Therefore, some of the essential oils that are both edible and have antimicrobial properties include cedar, cinnamon, citronella, clove, *eucalyptus*, garlic, geranium, lavender, lemon, lemongrass, mint, oregano, peppermint, rosemary, sesame and thyme oils.

Essential oils that are recognized by the US Environmental Protection Agency as minimum risk active pesticides under section 25(b) of the Federal Insecticide, Fungicide & Rodenticide Act (FIFRA) are cedar, cinnamon, citronella, clove, garlic, geranium, lemongrass, mint, peppermint, sesame, and thyme oils.

The antimicrobial properties of 21 essential oils and two plant essences were investigated against five food-borne pathogens. The maximum bacteriostatic concentration was 0.075%, with the oils of bay, cinnamon, clove and thyme being the most potent (ref: A. Smith-Palmer, J. Stewart and L. Fyfe. Antimicrobial properties of plant essential oils and essences against five important food-borne pathogens. Letters in Applied Microbiology 1998. 26. 118-122).

Oil of thyme, the essential oil of the common herb thyme (*Thymus vulgaris*), contains 20-54% thymol. Thyme essential oil also contains a range of additional compounds, such as p-cymene, myrcene, borneol and linalool. Before the advent of modern antibiotics, oil of thyme was used to medicate bandages. Thymol, a powerful antiseptic, is the main active ingredient in various commercially produced mouthwashes. Thymol has also been shown to be effective against various fungi that commonly infect toenails. Thymol can also be found as the active ingredient in some all-natural, alcohol-free hand sanitizers and hard surface disinfectants such as Scotch-Brite Disinfectant Wipes where the active ingredient is 0.05% thymol as a component of thyme oil.

Microemulsion technology has been in existence for many years. In fact, many commercial microemulsion products are found in the marketplace including floor polishes and cleaners, personal care products, pesticide delivery systems, cutting oils and drug delivery systems.

Microemulsions are crystal clear because the micellar particle size is too small to scatter visible light. The IUPAC definition of microemulsion is "a dispersion of water, oil and surfactant(s) that is an isotropic and thermodynamically stable system with dispersed domain diameter varying approximately from 1 to 100 nm, usually 10 to 50 nm." In contrast to ordinary, white macroemulsions that usually require high shear conditions to form, microemulsions form upon simple mixing of the components, without the need for high-energy homogenization. Also, microemulsions of the present inventions are stable against phase separation and remain crystal clear in both concentrated and ready to use form.

The processes of the present inventions produce novel, crystal clear, stable, oil-in-water microemulsions using only food grade or excipient grade surfactants, edible botanical extracts or essential oils, and distilled or deionized water. No alcohols or sugars are used or needed and there are no additives that are not food grade quality. The microemulsion compositions and the preparation method thereof provides high manufacturing efficiency and yield with no by-products, low toxicity, low production cost, simple preparation process, good safety in production, storage, transportation and use process, good environmental protection performance, are biodegradable and have excellent antimicrobial efficacy.

DESCRIPTION OF PRIOR ART

There exists a wealth of literature including many patents and patent applications dealing with the subject of microemulsions of essential oils. This literature can be grouped into two main end uses; edible microemulsions used to introduce essential oils into food and beverages and non-edible microemulsions used as antimicrobial disinfectants and cleaners.

For example, U.S. Pat. No. 4,835,002 granted to Wolf et al. teaches the manufacture of edible microemulsions of essential oils using a food grade surfactant and a polar alcohol such as ethanol, propylene glycol, glycerol, sugar or sugar alcohol in very high concentrations. The microemulsion is crystal clear and stable but there are no claims made for its use as an antimicrobial, but only as a beverage additive.

U.S. Pat. No. 5,376,397 assigned to Kraft Foods teaches the manufacture of edible microemulsion of flavor oils such as coffee oil that will not microemulsify using the surfactants and alcohols set forth in the above Wolf patent by using water immiscible alcohol (dodecanol). However, no antimicrobial claims are made.

U.S. Pat. No. 5,891,490 assigned to Nestles teaches the manufacture of edible microemulsion for coating food products that will brown in a microwave oven. However, no antimicrobial claims are made.

U.S. Pat. No. 6,902,756 assigned to Firmenick teaches the manufacture of transparent, high citrus oil loaded microemulsions for clear beverages that have excellent thermodynamic stability with over 30% oil loading and remain stable when diluted more than 100× in the final beverage. However, no antimicrobial claims are made.

WO2013075921 patent application assigned to Unilever N.V. teaches the manufacture of antimicrobial microemulsions of the essential oil components eugenol, turpinenol and thymol and a cationic surfactant selected from benzalkonium chloride or cetyltrimethyl ammonium bromide. Although an effective antimicrobial combination, only thymol is edible as a component of thyme oil.

EP2460409 patent application assigned to Nestec teaches the manufacture of a food grade emulsion of various antimicrobial essential oils using all food grade components including the oils and the gum acacia surfactant system. No claim is made the emulsions are clear microemulsion.

U.S. Pat. No. 8,417,877 assigned to Ohso Clean Inc teaches the manufacture of a stable microemulsion of thyme oil emulsified with alkylpolyglucocide or sodium lauryl sulfate but also contains cupric sulfate which has moderate human toxicity and is not a food additives.

U.S. Pat. No. 6,346,281 assigned to Scensible Life teaches the manufacture of an emulsion of thyme, lemongrass and *eucalyptus* oils using a small amount of ethanol and a biosurfactant but also contains one of cupric sulfate, cupric carbonate or colloidal silver, all considered moderately toxic and are not food additives.

In light of the above referenced patents and applications and all other not referenced literature, there is a clear and present need for an all food grade antimicrobial essential oil microemulsion that demonstrates excellent antimicrobial efficacy over a wide range of microbes, is stable for greater than one year without gaining turbidity or separating (ringing), is totally non-toxic to humans and animals and can be used around food preparation areas without concern for food contamination. It is an objective of this instant invention to provide such a process for the manufacture of same.

BRIEF SUMMARY OF THE INVENTION

This instant invention is a process for the manufacture of botanical antimicrobial microemulsions (BAMM) where the antimicrobial oils are chosen from the collective group of essential oils and extracts that are commonly obtained by steam distillation or cold pressing of stems, bark, leaves, fruit, peels and flowers of various plant species throughout the world. Some of the preferred essential oils used in the instant invention are derived from leaves that are edible herbs. Other preferred essential oils are extracted from the peels of citrus fruits that are used as flavorings for food and beverages. This source of antimicrobial oils is plentiful, renewable and generally regarded as safe, having low toxicity to humans and animals. The process of this invention teaches the manufacture of crystal clear, stable, edible microemulsions with essential oils that show no sign of clouding due to phase separation when aged at room temperature for >12 months at essential oil concentrations that allow for good transportation economics and excellent utility as hard surface disinfectants when further diluted to ready to use (RTU) strength.

DETAILED DESCRIPTION OF THE INVENTION

For purposes of demonstrating the process of this invention, the following essential oils and extracts were selected as preferred examples that are both antimicrobial and edible:

cinnamon, citronella, *eucalyptus*, geranium, lavender, lemongrass, peppermint and thyme oils and the orange peel extract d-limonene.

These essential oils are mainly produced in foreign countries and imported into the United States in drum or pail quantities, then repackaged and sold in quantities from a few grams to a few ounces at very high margins. There is no shortage of US sources who are providing this service on sites like Ebay and on-line stores. The essential oils for this invention were purchased from Wfmed, Lorton Va. 22079 and The Herbarie at Stoney Hill Farm, Inc. Prosperity, S.C. 29127. Both of these distributors of essential oils have excellent websites with lots of helpful literature including MSDS and specification sheets with ranges of the components that make up the standard of identities of the oils.

The surfactant system used to make crystal clear microemulsions of essential oils in water consists of 2 surfactants, an oil soluble and a water soluble surfactant. The oil soluble surfactant is Kolliphor EL, formerly known as Cremophor EL, and is the registered trademark of BASF Corp. for its version of polyethoxylated castor oil (POE(35) Castor oil). It is available from Mutchler Inc. in Harrington Park, N.J. It is prepared by reacting 35 moles of ethylene oxide with each mole of castor oil. The resulting product is a mixture (CAS number 61791-12-6) The major component is the material in which the hydroxyl groups of the castor oil triglyceride have been ethoxylated with ethylene oxide to form polyethylene glycol ethers. Minor components are the polyethylene glycol esters of ricinoleic acid, polyethylene glycols and polyethylene glycol ethers of glycerol. Kolliphor EL is a synthetic, nonionic surfactant with a hydrophile-lipophile balance (HLB) of 13.0 and its critical micelle concentration is 0.02%. Its utility comes from its ability to stabilize emulsions of nonpolar materials in aqueous systems. Kolliphor EL is an excipient or additive in drugs and is used to solubilize vitamins A, D, E & K. Therapeutically, modern drugs are rarely given in a pure chemical state, so most active ingredients are combined with excipients or additives such as Kolliphor EL.

The water soluble surfactant used to produce crystal clear microemulsions is Polysorbate 20 (polyoxyethylere (20) sorbitan monolaurate) and is available from ICI Americas as Tween 20 (CAS number 9005-64-5). The stability and relative non-toxicity of Tween 20 allows its use in a number of domestic and pharmacological applications including as a wetting agent in flavored cough drops and as an excipient in many prescription drugs. The World Health Organization has suggested acceptable daily intake limits of 0-25 mg of polyoxyethylene sorbitan esters per kg of body weight. The HLB of Tween 20 is 16.7 and its critical micelle concentration is 0.01%.

In addition to the above ingredients, a citric acid/sodium citrate buffer system is used to buffer system pH, provide an antioxidant to retard oxidation of system components and to contribute to antimicrobial efficacy. The dominant use of citric acid is as a flavoring and preservative in food and beverages, especially soft drinks. Citrate salts of various metals are used to deliver those minerals in a biologically available form in many dietary supplements. The buffering properties of citrates are used to control pH in household cleaners and pharmaceuticals. In the United States the purity requirements for citric acid as a food additive are defined by the Food Chemicals Codex, which is published by the United States Pharmacopoeia (USP).

Below is a typical formula for making a crystal clear, concentrated microemulsion from edible, antimicrobial essential oils in water using the above edible surfactant system.

| | |
|---|---:|
| Essential Oils (Total) | 11.8 g |
| Kolliphor EL | 12.0 |
| Water | 52.5 |
| Tween 20 | 21.5 |
| Citric Acid Monohydrate | 0.2 |
| Sodium Bicarbonate (10% in H2O) | 2.0 |
| Total | 100.0 g |

It has been determined that when preparing these microemulsions, order of addition is very important. The essential oils are first added to a dry mixing vessel followed by adding the Kolliphor EL which mixes in the essential to form a low viscosity, easily mixable, clear solution. This solution is heated to 65-75 C. In a separate vessel the water is added followed by Tween 20 and mixed to form a low viscosity, clear solution. Dry citric acid monohydrate is then dissolved in the aqueous solution and neutralized with 10% sodium bicarbonate to pH 5.7 to 6.0. The resultant buffered aqueous solution is heated to 65-75 C as well.

While the essential oils/Kolliphor EL solution is adequately mixing, the aqueous buffer/Tween 20 solution is added to the essential oils/Kolliphor EL. After all of the aqueous addition is complete, the system is agitated and cooled to 30-35 C. The product will be a crystal clear concentrated microemulsion of essential oils in water that is stable at room temperature indefinitely. The clarity will be <10 Nephelos Turbidity Units (NTU) using a Hach Ratio Turbidimeter. This is the "best mode" for carrying out the process of this invention.

The rate of aqueous addition is also dependent upon the essential oils being used. Some essential oils allow water addition times as rapid as less than one minute, while other systems require a longer water addition time. If any turbidity of the cooled product occurs, there is a good chance a microemulsion will not be formed to completion resulting in less than crystal clarity of the final dispersion. Cloudy microemulsions may be repaired to form clear microemulsions by post heating the fully diluted microemulsion to 65-75 C, then stopping the agitation and allowing the microemulsion to slowly cool to room temperature.

While the above "best mode" of operation represents the process for manufacturing a stable, antimicrobial, edible, crystal clear microemulsion concentrate at 11.8% essential oil that can be economically transported, this concentrate can be diluted with water using a ratio of 50 to over 100 parts (by wt.) of water to one part of concentrate using any order of addition, any temperature and any type of mixing to make the final "ready to use" (RTU) consumer product. For example, 8 g of concentrate can be added to 792 g of water in a 1 quart spray bottle, the bottle slowly shaken for ~10 seconds, and the result will be a fully uniform RTU microemulsion. The RTU product will also be a crystal clear, stable, water thin (easily sprayable) antimicrobial microemulsion that will not cloud upon aging. Current aging studies have been running over 1 year and these RTU products have remained crystal clear (<10 NTU) regardless of the essential oils used. This ease of dilution of the microemulsion concentrate and the subsequent stability of the highly diluted RTU product were unexpected and further demonstrates the unique nature of this process.

Essential oils can be used individually in the process of this invention or they can be used in combinations to generate unique and desirable fragrances. For example, many botanical antimicrobial emulsions are produced and marketed based on the powerful germicidal thymol which is a major component of thyme oil. As of 2014 there were 16 active EPA registrations under FIFRA for the use of thymol as the active ingredient in a germicidal emulsion at concentrations as low as 0.05% by weight of the emulsion. Most of these products use natural thymol as a component of thyme oil. However, thyme oil smells somewhat medicinal to many people who may prefer a citrus, mint or floral fragrance rather than a medicinal one. It is a further embodiment of this invention to use mixtures of various essential oils that provide both high antimicrobial broad spectrum efficacy while delivering a very pleasant aroma, similar to using essential oils for aromatherapy.

Several combinations of essential oils that have been converted to microemulsions using the process of this invention which improved the aroma of thyme oil are: Lavender/Lemongrass/Thyme, Cinnamon/Thyme and d-Limonene/Thyme. The use of d-limonene has the added economic advantage of much lower cost compared to essential oils, probably due to the glut of orange peels created by the orange juice industry and the ease of recovering and purifying d-limonene from the peels.

The dilution rate of the resultant concentrated microemulsion to RTU strength in the case of using combinations of essential oils that include thyme oil was calculated by determining the amount of water needed to dilute the thymol content to 0.05% by weight of the RTU product. This is based on analysis of label claims of EPA registered products listing thymol as the only active ingredient at 0.05%. For example, Scotch-Brite botanical disinfecting wipes claims "Kills over 99.9% of household germs: *Pseudomonas aeruginosa*, *Salmonella enterica*, *Staphylococcus aureus*, Methicillin Resistant *S. aureua* (MRSA), *Enterobact aerogenes*, Influenza A virus, Rhinovirus type 37, and Human Immunodeficiency Virus (HIV) type 1. Sanitizes hard non-porous, non-food contact surfaces of *Staphylococcus aureus* and *Enterobact aerogenes* in the presence of light to moderate soil load with a 30 second contact time".

Oil of Thyme can range from 20% to 54% thymol. So the thymol assay of the individual lot of thyme oil is needed along with the amount of thyme oil (weight %) used in the microemulsion in order to calculate the amount of dilution water that needs to be added to the concentrate to generate the RTU product. Therefore it is important to maximize the amount of thyme oil in the concentrated microemulsion while still incorporating enough of a more aromatic essential oil to give the end user a pleasant aroma during application. It is a further bonus that the choice of the more aromatic oil augments the broad spectrum antimicrobial efficacy of the RTU product.

Listed below are several, non-limiting examples of concentrated microemulsions prepared according to the detailed description of this invention that have a pleasant aroma in use, yet are high in thyme oil content as well as examples that are extremely economical to produce. These examples are provided to further augment the teachings of this invention and are not, in any way, to be misconstrued as limiting the scope of it

EXAMPLES

Example #1

Control for Improved Odor Examples 2 thru 6. Into a 250 ml Erlenmeyer was added 11.8 g of thyme oil (white *Thymus Zigus* at 50% thymol concentration) followed by 12.0 g of Kollophor EL. Moderate stirring produced a clear, thin solution at room temperature. Into a 200 ml beaker was added 52.5 g of distilled water followed by 21.5 g of Tween 20. Slightly longer mixing produced a clear, thin aqueous solution. To this aqueous solution was added 0.20 g of citric acid monohydrate crystals. Mixing continued until the crystals dissolved. A pH probe was inserted into the beaker and the pH of the aqueous mixture was neutralized from pH ~2 to pH 5.6 to 6.0 using 2.0 g of 10% aqueous sodium bicarbonate. The resultant buffered solution was clear and thin. Both the oil and aqueous solutions were heated simultaneously to 65-75 C in a microwave oven as measured by an infrared laser thermometer. The solutions were removed from the oven and the oil solution was magnetically stirred at moderate speed. The hot aqueous solution was slowly poured into the agitating oil solution over 30 to 60 seconds. When the addition was finished the resultant microemulsion was crystal clear and low in viscosity and was allowed to cool to 30-35 C with agitation using ambient air cooling. The cooled microemulsion was clear and was analyzed at 5 NTU using a Hach Ratio Turbidimeter. The bottled pack out yield was 99 g of concentrate. The concentrate remained at 5 NTU clarity when aged at 25 C for >12 months.

One g of concentrate was diluted with 117 g of distilled water to produce a clear, water thin RTU antimicrobial hard surface cleaner that had the following analysis: 0.05% thymol, pH 6.0, VOC content 0.1%, 0.34% total surfactant content, clarity of 3 NTU, clarity after 1 year aging at 25 C of 3 NTU with no phase separation; odor during use was medicinal.

Example #2

Into a 250 ml Erlenmeyer was added 9.65 g of thyme oil (white *Thymus Zigus* at 50% thymol concentration) and 2.15 g of cinnamon oil followed by 12.0 g of Kollophor EL. Moderate stirring produced a clear, thin solution at room temperature. Into a 200 ml beaker was added 52.5 g of distilled water followed by 21.5 g of Tween 20. Slightly longer mixing produced a clear, thin aqueous solution. To this aqueous solution was added 0.20 g of citric acid monohydrate crystals. Mixing continued until the crystals dissolved. A pH probe was inserted into the beaker and the pH of the aqueous mixture was neutralized from pH ~2 to pH 5.6 to 6.0 using 2.0 g of 10% aqueous sodium bicarbonate. The resultant buffered solution was clear and thin.

Both the oil and aqueous solutions were heated simultaneously to 65-75 C in a microwave oven as measured by an infrared laser thermometer. The solutions were removed from the oven and the oil solution was magnetically stirred at moderate speed. The hot aqueous solution was slowly poured into the agitating oil solution over 30 to 60 seconds. When the addition was finished the resultant microemulsion was crystal clear and low in viscosity and was allowed to cool to 30-35 C with agitation using ambient air cooling. The cooled microemulsion was clear and was analyzed at 6 NTU using a Hach Ratio Turbidimeter. The bottled pack out yield was 99 g of concentrate. The concentrate remained at 6 NTU clarity when aged at 25 C for >12 months with no phase separation.

One g of concentrate was diluted with 95.5 g of distilled water to produce a clear, water thin RTU antimicrobial hard surface cleaner that had the following analysis: 0.05% thymol, pH 5.7, VOC content 0.12%, 0.34% total surfactant content, clarity of 4 NTU, clarity after 1 year aging at 25 C of 4 NTU with no phase separation; odor during use was that of cinnamon.

Example #3

Into a 250 ml Erlenmeyer was added 9.1 g of thyme oil (white *Thymus Zigus* at 50% thymol concentration), 2.0 g of d-limonene and 0.7 g of orange oil followed by 12.0 g of Kollophor EL. Moderate stirring produced a clear, thin solution at room temperature. Into a 200 ml beaker was added 52.5 g of distilled water followed by 21.5 g of Tween 20. Slightly longer mixing produced a clear, thin aqueous solution. To this aqueous solution was added 0.20 g of citric acid monohydrate crystals. Mixing continued until the crystals dissolved. A pH probe was inserted into the beaker and the pH of the aqueous mixture was neutralized from pH ~2 to pH 5.6 to 6.0 using 2.0 g of 10% aqueous sodium bicarbonate. The resultant buffered solution was clear and thin.

Both the oil and aqueous solutions were heated simultaneously to 65-75 C in a microwave oven as measured by an infrared laser thermometer. The solutions were removed from the oven and the oil solution was magnetically stirred at moderate speed. The hot aqueous solution was slowly poured into the agitating oil solution over 30 to 60 seconds. When the addition was finished the resultant microemulsion was crystal clear and low in viscosity and was allowed to cool to 30-35 C with agitation using ambient air cooling. The cooled microemulsion was clear and was analyzed at 7 NTU using a Hach Ratio Turbidimeter. The bottled pack out yield was 99 g of concentrate. The concentrate remained at 7 NTU clarity when aged at 25 C for >12 months without any phase separation.

One g of concentrate was diluted with 90 g of distilled water to produce a clear, water thin RTU antimicrobial hard surface cleaner that had the following analysis: 0.05% thymol, pH 6.0, VOC content 0.13%, 0.34% total surfactant content, clarity of 5 NTU, clarity after 1 year aging at 25 C of 5 NTU with no phase separation; odor during use was citrus orange.

Example #4

Into a 250 ml Erlenmeyer was added 3.3 g of thyme oil (white *Thymus Zigus* at 50% thymol concentration) 2.2 g of lemongrass oil, and 6.3 g of Lavender oil followed by 12.0 g of Kollophor EL. Moderate stirring produced a clear, thin solution at room temperature. Into a 200 ml beaker was added 52.5 g of distilled water followed by 21.5 g of Tween 20. Slightly longer mixing produced a clear, thin aqueous solution. To this aqueous solution was added 0.20 g of citric acid monohydrate crystals. Mixing continued until the crystals dissolved. A pH probe was inserted into the beaker and the pH of the aqueous mixture was neutralized from pH ~2 to pH 5.6 to 6.0 using 2.0 g of 10% aqueous sodium bicarbonate. The resultant buffered solution was clear and thin.

Both the oil and aqueous solutions were heated simultaneously to 65-75 C in a microwave oven as measured by an infrared laser thermometer. The solutions were removed from the oven and the oil solution was magnetically stirred at moderate speed. The hot aqueous solution was slowly poured into the agitating oil solution over 30 to 60 seconds. When the addition was finished the resultant microemulsion was crystal clear and low in viscosity and was allowed to cool to 30-35 C with agitation using ambient air cooling. The cooled microemulsion was clear and was analyzed at 8 NTU using a Hach Ratio Turbidimeter. The bottled pack out yield was 99 g of concentrate. The concentrate remained at 8 NTU clarity when aged at 25 C for >12 months without any phase separation.

One g of concentrate was diluted with 32 g of distilled water to produce a clear, water thin RTU antimicrobial hard surface cleaner that had the following analysis: 0.05% thymol, pH 5.8, VOC content 0.36%, 0.34% total surfactant content, clarity of 7 NTU, clarity after 1 year aging at 25 C of 7 NTU with no phase separation; odor during use was lemon floral.

Example #5

Into a 250 ml Erlenmeyer was added 10.0 g of thyme oil (white *Thymus Zigus* at 50% thymol concentration) and 1.8 g of geranium oil followed by 12.0 g of Kollophor EL. Moderate stirring produced a clear, thin solution at room temperature. Into a 200 ml beaker was added 52.5 g of distilled water followed by 21.5 g of Tween 20. Slightly longer mixing produced a clear, thin aqueous solution. To this aqueous solution was added 0.20 g of citric acid monohydrate crystals. Mixing continued until the crystals dissolved. A pH probe was inserted into the beaker and the pH of the aqueous mixture was neutralized from pH ~2 to pH 5.6 to 6.0 using 2.0 g of 10% aqueous sodium bicarbonate. The resultant buffered solution was clear and thin.

Both the oil and aqueous solutions were heated simultaneously to 65-75 C in a microwave oven as measured by an infrared laser thermometer. The solutions were removed from the oven and the oil solution was magnetically stirred at moderate speed. The hot aqueous solution was slowly poured into the agitating oil solution over 30 to 60 seconds. When the addition was finished the resultant microemulsion was crystal clear and low in viscosity and was allowed to cool to 30-35 C with agitation using ambient air cooling. The cooled microemulsion was clear and was analyzed at 6 NTU using a Hach Ratio Turbidimeter. The bottled pack out yield was 99 g of concentrate. The concentrate remained at 6 NTU clarity when aged at 25 C for >12 months without any phase separation. One g of concentrate was diluted with 99 g of distilled water to produce a clear, water thin RTU antimicrobial hard surface cleaner that had the following analysis: 0.05% thymol, pH 6.0, VOC content 0.12%, 0.34% total surfactant content, clarity of 4 NTU, clarity after 1 year aging at 25 C of 4 NTU with no phase separation; odor during use was of roses.

Example #6

Into a 250 ml Erlenmeyer was added 10.0 g of thyme oil (white *Thymus Zigus* at 50% thymol concentration) and 1.8 g of d-limonene followed by 12.0 g of Kollophor EL. Moderate stirring produced a clear, thin solution at room temperature. Into a 200 ml beaker was added 52.5 g of distilled water followed by 21.5 g of Tween 20. Slightly longer mixing produced a clear, thin aqueous solution. To this aqueous solution was added 0.20 g of citric acid monohydrate crystals. Mixing continued until the crystals dissolved. A pH probe was inserted into the beaker and the pH of the aqueous mixture was neutralized from pH ~2 to pH 5.6 to 6.0 using 2.0 g of 10% aqueous sodium bicarbonate. The resultant buffered solution was clear and thin.

Both the oil and aqueous solutions were heated simultaneously to 65-75 C in a microwave oven as measured by an infrared laser thermometer. The solutions were removed from the oven and the oil solution was magnetically stirred at moderate speed. The hot aqueous solution was slowly poured into the agitating oil solution over 30 to 60 seconds. When the addition was finished the resultant microemulsion was crystal clear and low in viscosity and was allowed to cool to 30-35 C with agitation using ambient air cooling. The cooled microemulsion was clear and was analyzed at 6 NTU using a Hach Ratio Turbidimeter. The bottled pack out yield was 99 g of concentrate. The concentrate remained at 6 NTU clarity when aged at 25 C for >12 months without any phase separation. One g of concentrate was diluted with 99 g of distilled water to produce a clear, water thin RTU antimicrobial hard surface cleaner that had the following analysis: 0.05% thymol, pH 6.0, VOC content 0.12%, 0.34% total surfactant content, clarity of 4 NTU, clarity after 1 year aging at 25 C of 4 NTU with no phase separation; odor during use was light citrus orange.

TABLE I

Summary of Examples with Formula and Analysis

| | Ex. 1 Wt % | Ex. 2 Wt % | Ex. 3 Wt % | Ex. 4 Wt % | Ex. 5 Wt % | Ex. 6 Wt % |
|---|---|---|---|---|---|---|
| Ingredient | | | | | | |
| Thyme Oil | 11.80 | 9.65 | 9.10 | 3.30 | 10.00 | 10.00 |
| Cinnamon Oil | | 2.15 | | | | |
| d-Limonene | | | 2.00 | | | 1.80 |
| Rose Geranium Oil | | | | | 1.80 | |
| Lemongrass Oil | | | | 2.20 | | |
| Lavender oil | | | | 6.30 | | |
| Orange oil | | | 0.70 | | | |
| Kolliphor EL | 12.00 | 12.00 | 12.00 | 12.00 | 12.00 | 12.00 |
| Water | 52.50 | 52.50 | 52.50 | 52.50 | 52.50 | 52.50 |
| Tween 20 | 21.50 | 21.50 | 21.50 | 21.50 | 21.50 | 21.50 |
| Citric acid monohydrate | 0.20 | 0.20 | 0.20 | 0.20 | 0.20 | 0.20 |
| Sodium Bicarbonate (10% in H2O) | 2.00 | 2.00 | 2.00 | 2.00 | 2.00 | 2.00 |
| Total | 100.00 | 100.00 | 100.00 | 100.00 | 100.00 | 100.00 |
| Concentrate Analysis | | | | | | |
| Clarity (NTU) | 5 | 6 | 7 | 8 | 6 | 6 |
| Aging Stability at 25 C. (months) | >12 | >12 | >12 | >12 | >12 | >12 |
| RTU Analysis | | | | | | |
| Dilution Rate (per 1 pbw Conc) | 117 | 95.5 | 90 | 32 | 99 | 99 |
| Thymol wt. % | 0.050 | 0.051 | 0.051 | 0.052 | 0.051 | 0.051 |
| pH | 6.0 | 5.7 | 6.0 | 5.8 | 6.0 | 6.0 |
| VOC wt. % | 0.10 | 0.12 | 0.13 | 0.37 | 0.12 | 0.12 |
| Clarity (NTU No Change > 12 Mo) | 3.0 | 4.0 | 5.0 | 7.0 | 4.0 | 4.0 |
| Odor | Medicinal | Cinnamon | Orange | Citrus/Floral | Rose | Orange |

While the invention has been described with respect to specific examples, variations and modifications may be made without departing from the spirit and scope of the invention. Such variations and modifications are to be considered within the purview and scope of the invention as defined by the appended claims:

What I claim is:

1. A method forming a thermodynamically stable, oil-in-water, botanical antimicrobial microemulsion (BAMM) comprising;
   providing one or more antimicrobial, naturally derived, and edible essential oils and extracts and at least two naturally derived and edible, non-ionic surfactants, at least one of the surfactants an oil-soluble surfactant and at least one of the surfactants a water-soluble surfactant,
   mixing the one or more essential oils and extracts with the oil-soluble surfactant to form a first solution,
   diluting the water-soluble surfactant with water to form a second solution,
   adding a buffer to the second solution, forming a buffered solution, and
   combining the first solution with the buffered solution to produce an optically clear microemulsion that is stabilized from gaining turbidity and separating for at least one year.

2. The method of claim 1 wherein the one or more antimicrobial, naturally derived, and edible essential oils and extracts are selected from a group consisting of cedar, cinnamon, citronella, clove, *eucalyptus*, garlic, geranium, lavender, lemon, lemongrass, mint, orange, oregano, peppermint, rosemary, sesame and thyme oils and the orange peel extract d-limonene.

3. The method of claim 1 wherein both the surfactants used to form the BAMM are non-ionic and define a hydrophilic lipophilic balance (HLB) of 9 to 18, and wherein the total amount of surfactants used are from 1% to 50% of the total weight of the BAMM produced.

4. The method of claim 3 wherein the oil-soluble surfactant is non-hydrogenated polyoxyethylated castor oil and the water-soluble surfactant is polyoxyethylated sorbitan monolaurate.

5. The method of claim 1 wherein the buffer is dry citric acid monohydrate.

6. The method of claim 5 wherein the buffer is neutralized with 10% sodium bicarbonate.

7. The method of claim 1 wherein the BAMM is optically clear, with <10 Nephelos turbidity units [NTU], and stable for more than 12 months at 25 C without need for high sheer mixing equipment.

8. The method of claim 1, further comprising selecting one or more additional essential oils and extracts to supplement antimicrobial efficacy and aroma of the one or more essential oils and extracts, wherein the one or more essential oils and extracts is defined as thyme oil.

9. The method of claim 1 wherein the BAMM contains 10 to 15 wt. % essential oils.

10. The method of claim 1 further comprising diluting the BAMM with water and a food-grade, water-soluble diluent to define a concentration of all essential oils and extracts of 0.10% to 5 wt. %.

11. The method of claim 1 further comprising diluting the BAMM with water to define a concentration of all essential oils and extracts of 0.10% to 5 wt. %.

12. The method of claim 11 further comprising mixing the diluting water and the BAMM together with a low to moderate intensity mixer to form an optically clear and stable microemulsion.

13. The method of claim 11 wherein the concentration of essential oils and extracts is defined as 0.10% to 0.40% wt. essential oil relative to the total weight of the BAMM.

14. The method of claim 11 wherein the BAMM remains optically clear, with <10 Nephelos turbidity units [NTU], and stable after the diluting step without any oil/water separation for more than 12 months at 25 C.

15. The method of claim 11 wherein the BAMM contains at least 0.050% wt. thymol.

16. The method of claim 15 wherein the thymol is derived from thyme oil.

17. The method of claim 11 further comprising applying the BAMM to a surface as a disinfectant or deodorant to eliminate or inhibit odor and the growth of microorganisms.

* * * * *